United States Patent [19]

Fangrow, Jr. et al.

[11] Patent Number: 4,880,411
[45] Date of Patent: Nov. 14, 1989

[54] DISPOSABLE ASPIRATOR

[75] Inventors: Thomas F. Fangrow, Jr., Corona; Sam C. Lim, Santa Ana, both of Calif.

[73] Assignee: Life Support Products, Inc., Irvine, Calif.

[21] Appl. No.: 176,795

[22] Filed: Apr. 1, 1988

[51] Int. Cl.$^4$ .............................................. A61M 37/00
[52] U.S. Cl. ................................... 604/149; 251/343; 604/119; 604/246; 604/319
[58] Field of Search ........ 604/118, 119, 149, 317–319, 604/246, 247; 251/145, 319, 343, 344

[56] References Cited

U.S. PATENT DOCUMENTS

| | | | |
|---|---|---|---|
| 1,094,257 | 4/1914 | Schramm et al. | 604/149 |
| 2,253,143 | 8/1941 | Siegel | 604/149 |
| 2,509,671 | 5/1950 | Christensen | 251/344 |
| 2,900,978 | 8/1959 | Johannisson | 604/319 |
| 3,516,405 | 6/1970 | Hopper | 604/149 |
| 3,774,613 | 11/1973 | Woods, Jr. et al. | 604/149 |
| 4,275,731 | 6/1981 | Nichols | 604/319 |
| 4,419,093 | 12/1983 | Deaton | 604/319 |
| 4,650,470 | 3/1987 | Epstein | 604/149 |

FOREIGN PATENT DOCUMENTS 1096337 12/1967 United Kingdom ................ 251/343

OTHER PUBLICATIONS

Copy of Page from Emergency Medical Catalog entitled LSP Oxygen Delivery Equipment.

Primary Examiner—C. Fred Rosenbaum
Assistant Examiner—Mario Costantino
Attorney, Agent, or Firm—Knobbe, Martens, Olson & Bear

[57] ABSTRACT

An inexpensive, disposable aspirator is provided with a cover of unitary construction threadable onto a container for retaining body fluids removed from a patient. Instead of sterilizing the aspirator after the removal of body fluids, the aspirator is simply thrown away, thus minimizing contact with body fluids contaminated with infectious diseases such as AIDS. The aspirator is provided with a valve for controlling the flow of gas through the aspirator.

5 Claims, 1 Drawing Sheet

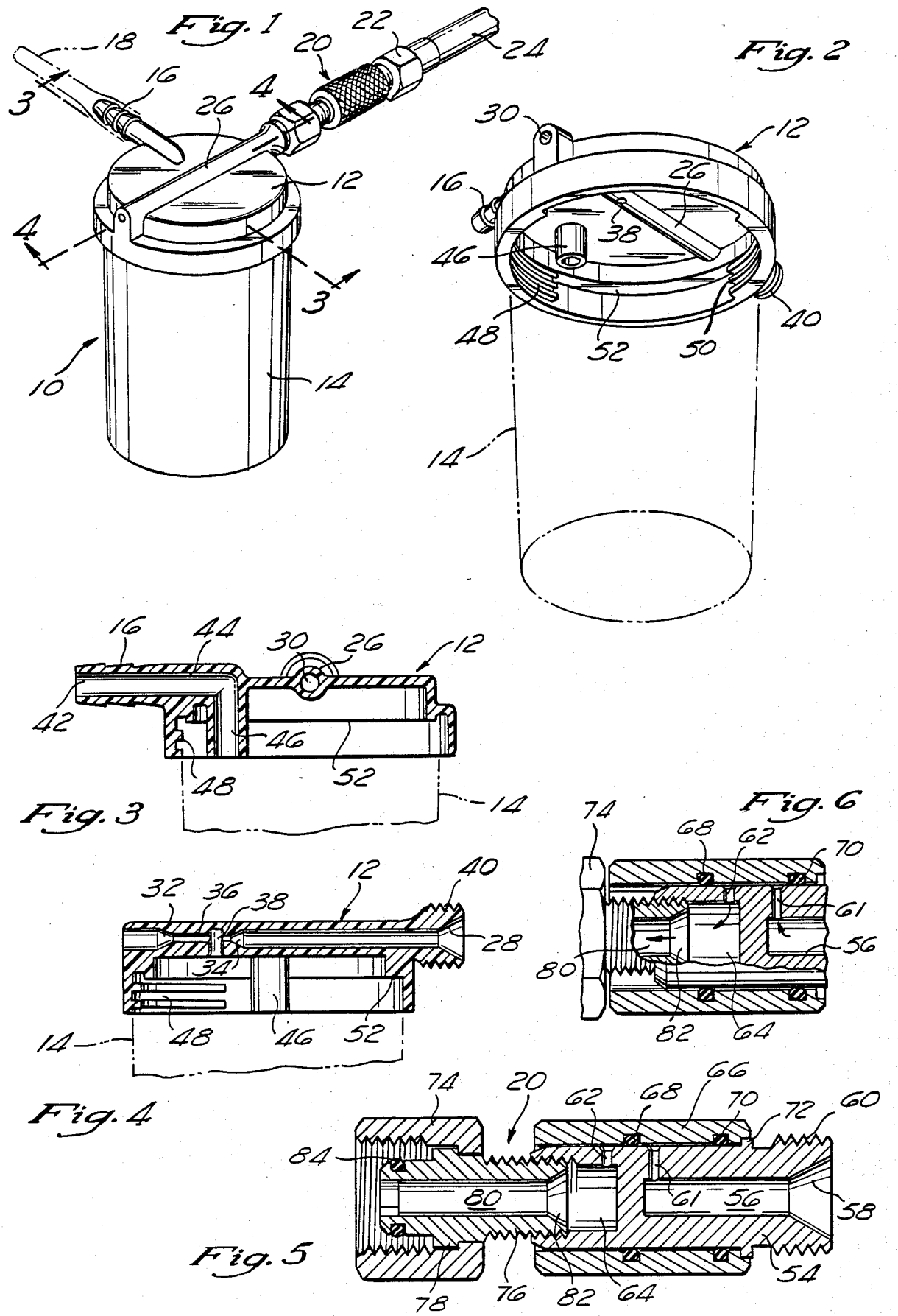

DISPOSABLE ASPIRATOR

BACKGROUND OF THE INVENTION

The present invention relates to aspirators for the removal of body fluids and foreign matter from the body, and in particular to a low-cost, disposable aspirator for minimizing the transmission of disease from a patient to another person.

Aspirators are used in hospitals and emergency rooms and by emergency rescue squads in the field for the removal of mucus, vomitus, other body fluids, and foreign matter from a patient by suction. Such an aspirator includes a venturi which is connected to a source of pressurized gas such as air or oxygen in order to produce a partial vacuum which enables a flexible hose to draw in the material to be removed from the patient.

One prior art aspirator includes a cover having a fluid inlet and a fluid outlet and a venturi and a valve fluidly connected between the inlet and the outlet. The cover is threadable onto a cylindrical container for retaining body fluids and other matter removed from a patient. The fluid passageway between the inlet and outlet in the cover contains a hole in fluid communication with the cylindrical container so that when pressurized air or other gas is supplied to the fluid inlet and flows through the venturi to the fluid outlet, a partial vacuum is produced inside the container. The valve is connected inline with the first fluid path so that the path may be either opened or closed.

The cover contains a second fluid path which connects a second fluid inlet with the interior of the container. A flexible hose is attachable this second fluid inlet so that body fluids and other material to be removed from a patient are drawn into the cylindrical container by the hose when the partial vacuum is produced by the venturi.

The cover of the prior art aspirator described above is relatively complicated and includes approximately 20 different parts including seven O-rings, a spring, a set screw, tubular inserts, etc. Because the parts need to be separately manufactured and then assembled, the aspirator is relatively expensive and is not disposable after it is used. As a result, after each use the aspirator needs to be sterilized. This sterilization requires disassembly of the aspirator which increases the risk that medical personnel responsible for sterilization will come into contact with body fluids contaminated with fluid-communicable diseases such as acquired immune deficiency syndrome (AIDS).

SUMMARY OF THE INVENTION

The present invention is directed to a low-cost aspirator which can be discarded after it is used. As a result, there is no need to sterilize the aspirator, thus saving valuable medical personnel time. Also, since the aspirator is not sterilized but simply discarded, there is no need for medical personnel to handle the parts of the aspirator which have been exposed to body fluids which may contain a deadly contaminant such as the AIDS virus.

In one embodiment of the invention, the aspirator comprises a unitary cover formed of plastic which is threadable onto a cylindrical plastic container which receives the body fluids drawn in by the aspirator. Since the cover is unitary, there is no need for the manufacture and assembly of a plurality of different parts. After each use, the contaminated aspirator is simply discarded without unscrewing the cover from the container and thus eliminates exposure to possible deadly body fluids which would necessarily occur if the cover were unscrewed from the container in order to sterilize the aspirator.

Another aspect of the invention is a reusable valve connected upstream of the aspirator. The valve has a pair of connectors of the same diameter so that the valve may be inserted between the aspirator and the pressurized gas supply line for supplying gas to the aspirator venturi without the need for a special adapter. Also, since the valve is connected upstream of the aspirator, the valve is not contaminated by body fluids during the operation of the aspirator.

These and other objects, features, and advantages of the present invention will be apparent in view of the following detailed description of a preferred embodiment, which is explained with reference to the figures, a brief description of which is provided below.

BRIEF DESCRIPTION OF THE DRAWINGS

FIG. 1 is a perspective view of a disposable aspirator connected to a valve and a flexible hose in accordance with the invention;

FIG. 2 is a perspective view of the underside of the cover of the disposable aspirator;

FIG. 3 is a cross-sectional view of the cover of the aspirator taken along lines 3—3 in FIG. 1;

FIG. 4 is a cross-sectional view of the cover of the aspirator taken along lines 4—4 in FIG. 1;

FIG. 5 is a cross-sectional view of a valve connectable to the aspirator in a closed position; and FIG. 6 is a cross-sectional view of a valve connectable to the aspirator in an open position.

DETAILED DESCRIPTION OF A PREFERRED EMBODIMENT

An aspirator 10 in accordance with the invention is shown in FIG. 1. The aspirator includes a threaded cover 12 and a cylindrical container 14 into which body fluids are drawn during operation of the aspirator. The cover 12 has a ribbed arm 16 to which one end of a flexible hose 18 may be attached. The other end of the flexible hose 18 is manipulated by the user of the aspirator to draw body fluids or foreign substances from a patient into the container 14. The cover 12 is attached to a valve 20 which is attached to a source of pressurized gas, which may be oxygen or air, for example, via a threaded female connector 22 coupled to a gas supply hose 24. As described below, the valve 20 is movable to one position in order to supply gas to the aspirator 10 and another position in order to cut off the flow of gas.

A cylindrical conduit 26 is integrally formed with the cover 12 and defines a first fluid flow path having a fluid inlet at a frustoconical bore 28 (shown in FIG. 4) fluidly coupled to the valve 20 and a fluid outlet 30 vented to the atmosphere. This first fluid path produces the partial vacuum in the container 14. A cross-section of the cover 12 is shown in FIG. 4. Now referring to FIG. 4, the conduit 26 includes a venturi comprising a pair of frustoconical bores 32, 34 which connect a cylindrical channel 36 having a diameter narrower than that of the remainder of the conduit 26. A cylindrical bore 38 is transversely formed in the narrowed channel 36 from the underside of the cover 12 so that the narrowed channel 36 is in fluid communication with the interior of the container 14. The cylindrical conduit 26 is integrally formed with a threaded male connector 40 in which the frustoconical bore 28 is formed.

Now referring to FIG. 3, the cover 12 includes another flow path defined by a bore 42 in the ribbed arm 16 and a conduit 44 formed in and lying in the plane of the cover 12. This conduit 44 is fluidly connected to a second conduit 46 extending vertically into the container 14. When a partial vacuum is produced in the interior of the container 14, body fluids are drawn into the container 14 from the ribbed arm 16 via the two conduits 44, 46.

As shown in FIG. 2, the interior of the cover 12 has two threaded portions 48, 50 which facilitate the threading of the cover 12 onto the container 14. When the cover 12 is screwed tightly onto the container 14, an annular ridge 52 in the cover 12 seats firmly against a rubber gasket (not shown) provided around the top edge of the container 14, thus preventing the contents of the container from leaking. If additional thread strength is desired, a full thread on a metal threaded insert may be provided inside the cover 12 instead of the threaded portions 48, 50.

An important feature of the aspirator 10 just described is that the cover 12 is of unitary construction. In particular, all parts of the cover 12 including the conduits 26, 44, 46, the venturi, the male connector 40, etc. are formed from a single piece of plastic such as glass-filled polypropylene, by injection molding, for example. As a result, an extremely inexpensive aspirator is produced which can be economically discarded after it is used.

Another aspect of the invention is the valve 20 connected between the conduit 26 and the gas supply hose 24. The valve 20, the detailed structure of which is shown in FIG. 5, includes a cylindrical tube 54, preferably of brass, having a first fluid inlet fluidly coupled to a bore 56 with a frustoconical opening 58 formed in a threaded male connector 60 integrally formed with the tube 54. The cylindrical tube 54 also has a fluid outlet terminating at one or more bores 61 general to the bore 56, a second fluid inlet at one or mores bores 62 parallel to but spaced from the bore 61, and a second fluid outlet at a bore 64. The bores 61, 62 have small frustoconical portions on their ends.

The terms "inlet" and "outlet" as used herein, which are dependent upon the direction of fluid flow, are used to describe the valve 20 when it is connected to the aspirator 10 and the gas supply hose 24 shown and described herein.

Now referring again to FIG. 5, the valve 20 includes a generally cylindrical sleeve 66 which surrounds and is slidable on the tube 54. The sleeve 66 is preferably formed of aluminum alloy. The internal diameter of the sleeve 66 is slightly larger than the outside diameter of the tube 54 so that gas may flow between the tube 54 and the sleeve 66. Two annular grooves are formed in the sleeve 66 and a pair of silicon O-rings 68, 70 are provided in the grooves.

The sleeve 66 is slidable on the tube 54 between an open position and a closed position. The valve 20 in FIG. 5 is shown in its closed position. In this position, the sleeve 66 abuts a raised annular stop 72 formed integrally with the tube 54, and the O-ring 68 prevents gas flow between bores 61, 62. The sleeve 66 is slidable to an open position, which is shown in FIG. 6, in which the sleeve 66 abuts a threaded female connector 74. In this open position, the bores 61, 62 are located in between the O-rings 68, 70, and since the inside diameter of the sleeve 66 is slightly larger than the outside diameter of the tube 54, gas flows from the bore 61 to the bore 62 in the direction of the arrows. The O-rings 68, 70 may be coated with a suitable lubricant to facilitate their sliding on the tube 54.

Now referring back to FIG. 5, the end of the tube 54 adjacent the bore 64 is threaded to receive a connector 76 having a raised annular stop 78 which retains the threaded female connector 74 on the connector 76. Teflon tape may be provided on the threads of the connector 76 to form a desired seal. The connector 76 has a cylindrical bore 80 therethrough and a frustoconical bore 82 which are both fluidly coupled to the bore 64. An O-ring 84 is provided on the end of the connector 76.

When the valve 20 is attached to the aspirator 10, the threaded male connector 40 (FIG. 4) is threaded into the connector 74 (FIG. 5) until the interior surface of the frustoconical bore 28 is seated tightly against the O-ring 84 on the connector 76 of the valve 20. The other end of the valve 20 is connected to the gas supply hose 24 by screwing the threaded female connector 22 of the gas supply hose 24 onto the threaded male connector 60 of the valve 20.

One of the advantages of the invention is that the valve 20 can be provided in-line with the gas supply line 24 and without the need for a special adapter. In this regard, the internal threaded diameter of the female connector 74 being substantially the same as the outer threaded diameter of the male connector 60.

In use and operation, the aspirator 10 is attached to the valve 20 and the gas supply line 24 as just described. Before aspiration begins, the valve 20 is moved to its closed position as shown in FIG. 5 so that gas from the source of pressurized gas is not wasted. In order to commence aspiration, the user slides the sleeve 66 to its open position as shown in FIG. 6, and then moves the flexible hose 18 to the area of the patient's body from which the body fluids or foreign matter are to be removed.

When the valve 20 is opened, pressurized gas will be supplied by the gas supply hose 24 through the valve 20 and the venturi in the conduit 26 to the fluid outlet 30 vented to the atmosphere. When it passes through the venturi, the gas will create a partial vacuum in the container 14 which will produce suction on the flexible hose 18 since it is in fluid communication with the interior of the container 14. As a result, the body fluids and other matter to be removed will be drawn into the container 14.

After the user has finished removing all of the body fluids he wishes to remove, the valve 20 is shut off by sliding the sleeve 66 to its closed position as shown in FIG. 5. The user may then remove the valve 20 from the aspirator 10 by unscrewing the female connector 74 from the male connector 40. Neither these connectors 40, 74 nor the valve 20 will be contaminated with body fluids since these parts are relatively isolated from the interior of the container 14 and are located "upstream" of the aspirator 10. Thus, the user will not need to worry about being infected with AIDS or other infectious diseases by coming into contact with the contaminated fluids.

After the aspirator 10 has been removed from the valve 20, the aspirator 10, including the hose 18, can be thrown away without unscrewing the container 14, in which the contaminated fluids are sealed. Since the aspirator is thrown away, no sterilization is necessary.

In addition, and more importantly, the risk of contracting an infectious disease such as AIDS is minimized if not eliminated since sterilization would require the disassembly of a contaminated prior art aspirator with the resultant chance that the contaminated fluids would come in contact with the skin or body fluids of the medical personnel responsible for sterilization.

Modifications and alternative embodiments of the invention will be apparent to those skilled in the art in view of the foregoing description. Accordingly, this description is to be construed as illustrative only, and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A disposable aspirator, comprising:
   a plastic container having an open upper end;
   a generally flat cover which mates with the open end of said container to close the container;
   a gas flow tube formed unitary with said cover and extending diametrically across said cover in the general plane of the cover, said tube having a gas inlet end formed unitary with an enlarged connector that extends radially beyond the periphery of said cover, said tube further having an outlet end opposite from said inlet end and terminating substantially flush with the exterior of said cover;
   a venturi positioned within said tube coaxial with said tube and having a restrictor section of reduced interior diameter, said venturi restrictor section being positioned much closer to said tube outlet than to said tube inlet;
   said tube having a venturi opening formed therein extending from said restrictor section and opening into said container to form a flow path so that, when high velocity fluid flows through said tube and restrictor section, a vacuum is formed within said container; and
   a fluid suction conduit formed unitary with said cover, said conduit forming a flow path between the interior of the container and the exterior of the container, whereby the vacuum within the container may be applied to a fluid outside of the container to draw the fluid into the container, said conduit including a fluid inlet portion having its axis generally in the plane of said cover, said conduit inlet portion having an inlet end which extends radially beyond the periphery of the cover and is adapted to be connected to tubing for aspirating fluids into the container, said conduit further including an outlet portion which extends downwardly towards the interior of the container, said outlet portion including an upper end which joins with said inlet portion and a lower outlet end which opens into the container, said conduit outlet portion being positioned between and spaced from the upper end of the container and said gas flow tube.

2. The aspirator of claim 1, wherein said tube exterior diameter is significantly greater than the thickness of said cover such that elongated curved exterior portions of said tube protrude beyond the upper surface of said cover and beyond the lower said surface of the cover, said conduit inlet portion having a diameter greater than the thickness of the cover so that curved exterior portions of said conduit inlet portion extend above the upper surface of the cover and below the lower surface of the cover.

3. The aspirator of claim 1, wherein said venturi is formed unitary with said tube.

4. An aspirator as defined in claim 1 additionally comprising a valve in fluid communication with said first fluid flow path, said valve comprising:
   a tube having a first fluid flow path including a first fluid inlet and a first fluid outlet and a second fluid flow path including a second fluid inlet and a second fluid outlet; and
   a sleeve having a bore therethrough, a portion of said bore having a diameter that is larger than the external diameter of said tube to allow gas to flow in said portion of said bore, said sleeve being slidable on said tube to occupy a first position in which said portion of said bore is in fluid communication with both said first fluid outlet and said second fluid inlet whereby gas is allowed to flow from said first fluid inlet to said first fluid outlet to said second fluid inlet to said second fluid outlet and a second position in which said portion of said bore is not in fluid communication with both said first fluid outlet and said second fluid inlet.

5. An aspirator as defined in claim 4 wherein the exterior of said tube and the interior of said sleeve are substantially cylindrical.

* * * * *